United States Patent [19]

Berger

[11] Patent Number: Plant 7,328

[45] Date of Patent: Sep. 18, 1990

[54] APPLE TREE: EARLY SPUR ROME

[75] Inventor: Wilfred M. Berger, Quincy, Wash.

[73] Assignee: Columbia and Okanagan Nursery Company, Wenatchee, Wash.

[21] Appl. No.: 299,947

[22] Filed: Jan. 23, 1989

[51] Int. Cl.[5] ..... A01H 5/00

[52] U.S. Cl. ..... Plt./34

[58] Field of Search ..... Plt./34

[56] References Cited

U.S. PATENT DOCUMENTS

| | | | |
|---|---|---|---|
| P.P. 1,550 | 1/1957 | Law | Plt. 34 |
| P.P. 3,121 | 4/1972 | Taylor | Plt. 34 |
| P.P. 4,096 | 8/1977 | Simmons | Plt. 34 |
| P.P. 4,793 | 11/1981 | Simmons | Plt. 334 |
| P.P. 4,974 | 1/1983 | Taylor | Plt. 34 |

*Primary Examiner*—James R. Feyrer

*Attorney, Agent, or Firm*—Klarquist, Sparkman, Campbell, Leigh & Whinston

[57] ABSTRACT

A new variety of Rome apple tree has dense foliage and fruit which takes on a red color early in its development and which ripens early.

2 Drawing Sheets

The present invention relates to a new and distinct variety of Rome apple tree. I have named my new variety "Early Spur Rome".

While caring for our orchard located in Quincy, Wash., my attention was attracted to three trees growing in a cultivated area in a block of Law Spur Rome trees I had purchased some time before from an apple tree supplier. The first year that this block of trees bore some scattered fruit, I noticed that apples on these three trees colored earlier than the apples of other trees of the Law Spur Rome variety growing in same block of trees. In addition, I noticed that the fruit on these three trees assumed their full finished color approximately seven to ten days ahead of the fruit on the rest of the Law Spur trees. These three trees apparently resulted from grafts of a common limb sport of the Law Spur Rome variety. However, the exact parentage of these trees cannot be determined with certainty.

Continued observation of these three trees over the next several years confirmed these observations that my Early Spur Rome variety bore fruit which colors earlier and assumes its full finished color earlier than apples of the standard Law Spur Rome trees. In addition, I also observed that blooms on my Early Spur Rome variety appear approximately two days ahead of blooms on the Law Spur Rome trees. Also, the trees of my new variety seem to have a denser foliage, with less dead spur wood, than I have observed in the standard Law Spur Rome trees growing in my orchard. Furthermore, even at the center of these Early Spur Rome trees, where very little sunshine penetrates, the apples still color extremely well and uniformly. In comparison, the apples at the center of Law Spur Rome trees remain much lighter, due to receiving less sunlight than those located at the outside of the trees. Another difference I have observed is that the standard Law Spur Rome apples contain an oval core while apples of my Early Spur Rome variety have a heart-shaped core. Moreover, apples from my Early Spur Rome trees, when cut open, do not have red color in their vascular cells. Otherwise, my Early Spur Rome tree, insofar as I have observed as of this time and except as explained below, has characteristics which are like those of the Law Spur Rome tree.

Close observations of these three Early Spur Rome trees, and continued observations of progeny thereof subsequently asexually propagated under my direction by grafting, has confirmed that the unique characteristics of my new variety are indeed different from prior varieties of Rome apple trees of which I am aware. These three Early Spur Rome trees have been repeatedly observed to be identical, one to the next. These observations were made with the three trees on the same understock. I am therefore convinced that my new tree represents a new and improved variety of Rome apple tree, as particularly evidenced by the following unique combination of characteristics, which have proven firmly fixed, are outstanding therein, and which distinguish it from other varieties of this species:

1. Apples which assume a red coloration early in development and which reach their full finish red color earlier than apples of other known Rome apple trees;
2. Apples with a heart-shaped core;
3. Foliage which is relatively dense; and
4. Blossoms which tend to appear slightly earlier than blossoms of Law Spur Rome trees.

The accompanying photographs depict the color of the fruit and foliage of my new variety as nearly true as is reasonably possible to make the same in a color illustration of this character.

FIG. 1 is a color photograph of a second generation tree of my invention showing the dense foliage of this tree;

FIG. 2 is a color photograph of two apples of a tree of my variety, the photograph having been taken on July 28th, 1987, with an apple from a Law Spur apple tree being held by hand in the photograph to show the difference in coloration at this stage of development of the apples;

FIG. 3 is a photograph of apple bearing limbs of my new variety taken on June 17th, 1988, again showing the early red color achieved by apples from my variety of tree and also showing two apples from a Law Spur Rome tree to again show the difference in coloration achieved by these varieties;

FIG. 4 is a photograph of an apple from a tree of my new variety which has been cut in half to show the heart-shaped core of the apple; and FIG. 5 is a photograph of leaves from my new variety illustrating the red stem vein at the underside of the leaves.

As previously mentioned, one of the primary distinguishing features of my new variety of apple tree over other Rome apple tree varieties is the early red coloration of apples on my new tree and the more rapid finish coloration of these apples. This is extremely advantageous as apples from my Early Spur Rome tree can reach the market earlier than apples from other Rome apple tree varieties.

The photographs of FIGS. 2 and 3 clearly illustrate this difference in coloration between apples of my new variety and those of the standard Law Spur Rome variety. In contrast to FIGS. 2 and 3, which show apples of my new variety starting to reach their full color in June and July in Quincy, Wash., in general, Rome apples of other varieties grown in this area do not start to achieve their full color until about the first or middle of September. The finish color of apples of my new variety is, however, similar to the finish color of apples from Law Spur Rome trees except that the apples of my new variety seem to have a slightly deeper red color than apples of the Law Spur variety and virtually the entire skin surface apples of my new variety, including the stem of basin area, has a uniform red ground finish color. Thus, the finish color of apples of my new variety is a continuous uniform blush without striping. In comparison, the stem or basin area of Law Spur apples which have achieved their finish color typically have a green coloration.

The photograph of FIG. 5 illustrates the red color of the stem vein of the underside of the leaves of my new variety. Law Spur Rome trees have not been observed by the inventor to have leaves with stem veins of this color.

A comparison of apple picking dates of Law Spur Rome trees and Early Spur Rome trees growing in the same area in my orchard in Quincy, Wash. in 1985, 1986 and 1987 also confirms this difference. The respective picking dates for apples from my Early Spur Rome trees were Sept. 30th, 1985; Sept. 28th, 1986 and Oct. 1st, 1987. In comparison, the picking dates for apples from the Law Spur Rome trees were Oct. 9th, 1985; Oct. 8th, 1986 and Oct. 12th, 1987.

A comparison was made of the internode lengths, spur characteristics and branching habit of three trees of my new variety with three trees of the Law Spur variety with the results summarized below:

| | Early Spur Rome Variety | Law Spur Rome Variety |
|---|---|---|
| Spur density per foot of 2 year old wood | 10 or 11 | 5 or 6 |
| Occurences and location of fruit spurs | Prolific on 2 year old wood including Central Leader Less than 10% Blindwood | disturbed on 2-4 year old wood, although some 2 tear wood lacks heavy spur production 25% to 30% Blindwood |
| Internode Lengths | 1-2" on spurs 2-4" on branches 1" on 1 year old wood | 2-3" on spurs 2-4" on branches 1-2" on 1 year old wood |
| Branching Habit | Alternate | Upright growth |

-continued

| | Early Spur Rome Variety | Law Spur Rome Variety |
|---|---|---|
| | Crotch angle greater than 45° Branching on trees appears to be predominately flat with few or no upright sprouts | Crotch angle of about 45° or less |

On Sept. 12, 1989, a comparison was made of apples from Early Spur Rome variety with apples from the Law Spur Rome variety. At that time, the Early Spur Rome apples had achieved 100% of their finished color while the Law Spur Rome apples had achieved about 65% of their finished color. This again confirms the earlier coloring of apples of my new variety. In addition, a sugar content comparison of apples was made at this time, along with a pressure comparison, with the following results:

Sugar Content and Pressure Comparison

| Early Spur Rome (With Ethrel) | Early Spur Rome (Without Ethrel) | Law Spur Rome |
|---|---|---|
| 12.5 Sugar | 10.8 Sugar | 9.5 Sugar |
| 13.0 Sugar | 11.5 Sugar | |
| 22 pounds | 22 pounds | 24 pounds |
| 23 pounds | | |

This earlier coloration of the Early Spur Rome variety is extremely beneficial. That is, because the new variety achieves its color early, the desired color is achieved before the fruit matures for picking. The maturation of the fruit can then be monitored and, for example, when it is at the desired level for optimum picking for long-term storage, the fruit can be picked because it has already achieved its desired color. In addition, with the new variety, chemicals such as Ethrel may optionally be used to advance the maturity of apples of the new variety after they have achieved full color. The use of such chemicals advances the picking date of the new variety even further ahead of the picking date of the Law Spur Rome fruit. In comparison, Law Spur Rome apples, typically reach optimum maturity for purposes of long-term storage before achieving their desired full finish color. Consequently, these varieties tend to become over mature for purposes of long-term storage while waiting for them to achieve their finish color. Chemicals such as Ethrel typically would not be used with Law Spur Rome fruit, as the problem with the maturation of this fruit before coloration would worsen if these chemicals were used.

The following is a detailed description of my new variety of Early Spur Rome apple tree. Except for the leaf stem color, colors are not identified in this description by Royal Horticultural Colour Chart plates because the colors are like those, insofar as I have determined, of Law Spur Rome apple trees.

Variety: Early Spur Rome.

Parentage: Believed to be a Limb Sport of a Law Spur Rome tree.

Locality where grown and observed: Quincy, Wash.

Dates of picking: Late September and Early October in Quincy, Wash.; typically about seven to ten days ahead of the Law Spur Rome trees growing in the same area.

Size:

*Medium.*—Observed as of this time to be like that of Law Spur Rome cultivar.

Tree:

*Vigor.*—Moderately vigorous; moderate grower; hardy.

*Habit.*—Spreading; dense; vase formed.

*Productivity.*—Very productive, but a somewhat uncertain bearer.

*Fruit.*—Well distributed.

*Trunk.*—Medium.

*Branches.*—Slender; smooth; much branching; red-brown in color (like Law Spur Rome variety).

*Lenticels.*—Medium number; medium size.

*Leaf.*—Like Law Spur variety — small size; long with medium width; somewhat U-folded; oval; medium density when compared to the species, but visually appears to be of a higher density than the Law Spur cultivar; apex acute — tapered; light green in color; medium thickness; smooth; finely serrate margin; medium length and medium thick petioles; red vein stem like RHS 53B, which becomes progressively more apparent as the leaves mature.

Flowers:

*Color.*—White-pink, like Law Spur Rome variety.

*Size.*—Large, like Law Spur Rome variety.

*Bloom date.*—Observed to appear approximately two days ahead of blooms on the Law Spur Rome trees.

Fruit:

*Skin.*—Thick; tough. Color of dots — whitish yellow. Distribution of dots — irregular. Ground color of finished fruit like RHS 187B, similar to but slightly deeper red in color than the color of fruit of the Law Spur variety. The general finish color effect is 100% red at maturity, including the stem or basin area of the fruit and the area surrounding the calyx of the fruit.

*Core.*—Heart-shaped.

*Quality.*—Flesh of the fruit is white, hard with a fine texture, and juicy; flavor of the fruit is somewhat subacid and flat.

*Shelf-life.*—Good.

Except as explained above and in particular with respect to the earlier coloration and ripening, the fruit insofar as I have been able to observe is like the fruit of the Law Spur Rome variety.

I claim:

1. A new and distinct variety of apple tree, substantially as herein shown and described, characterized by its dense foliage and fruit which takes on a red color early in its development and which ripens early.

* * * * *

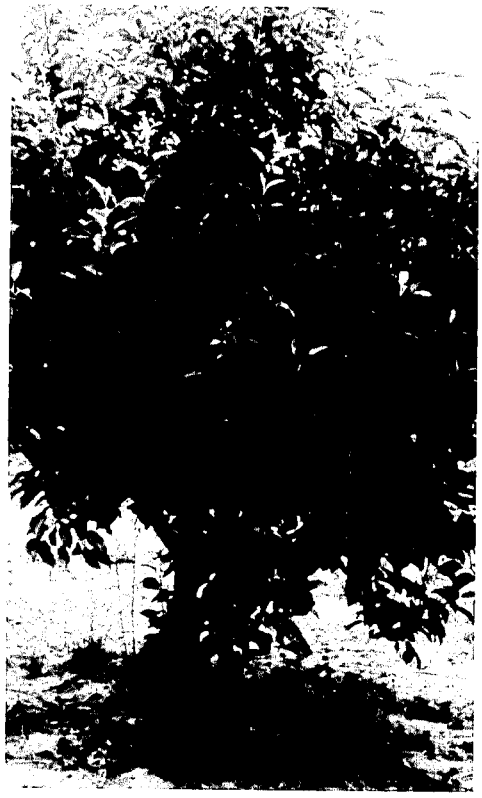
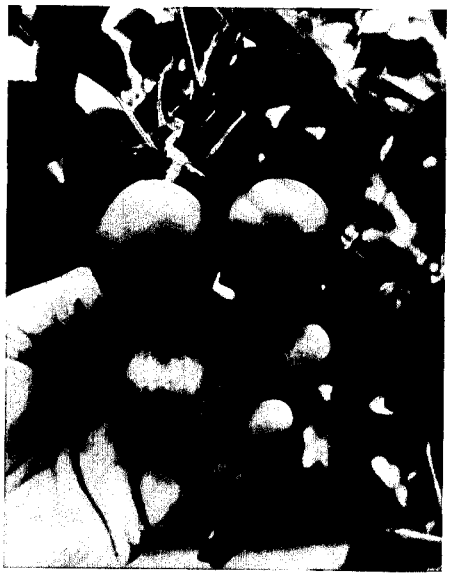
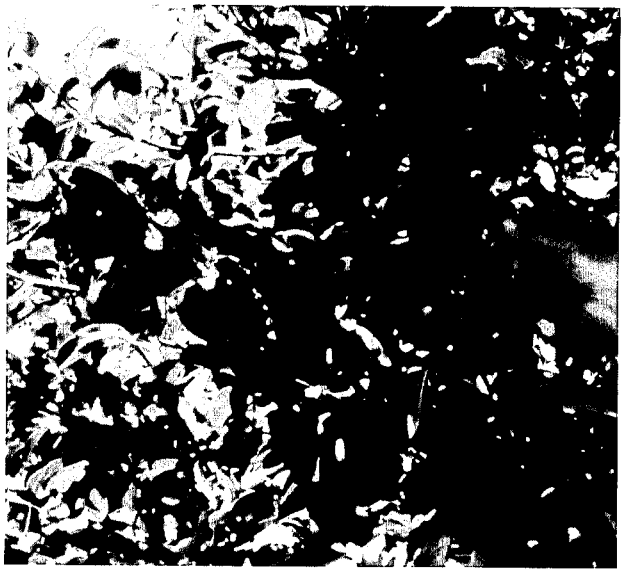
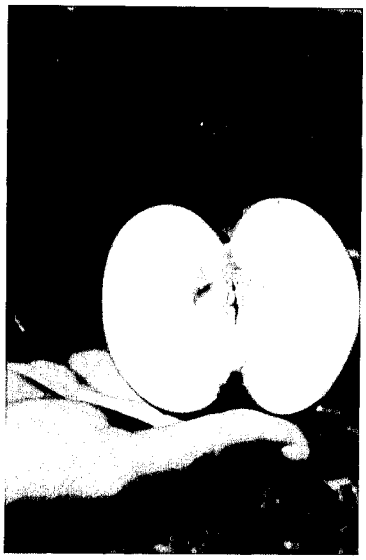

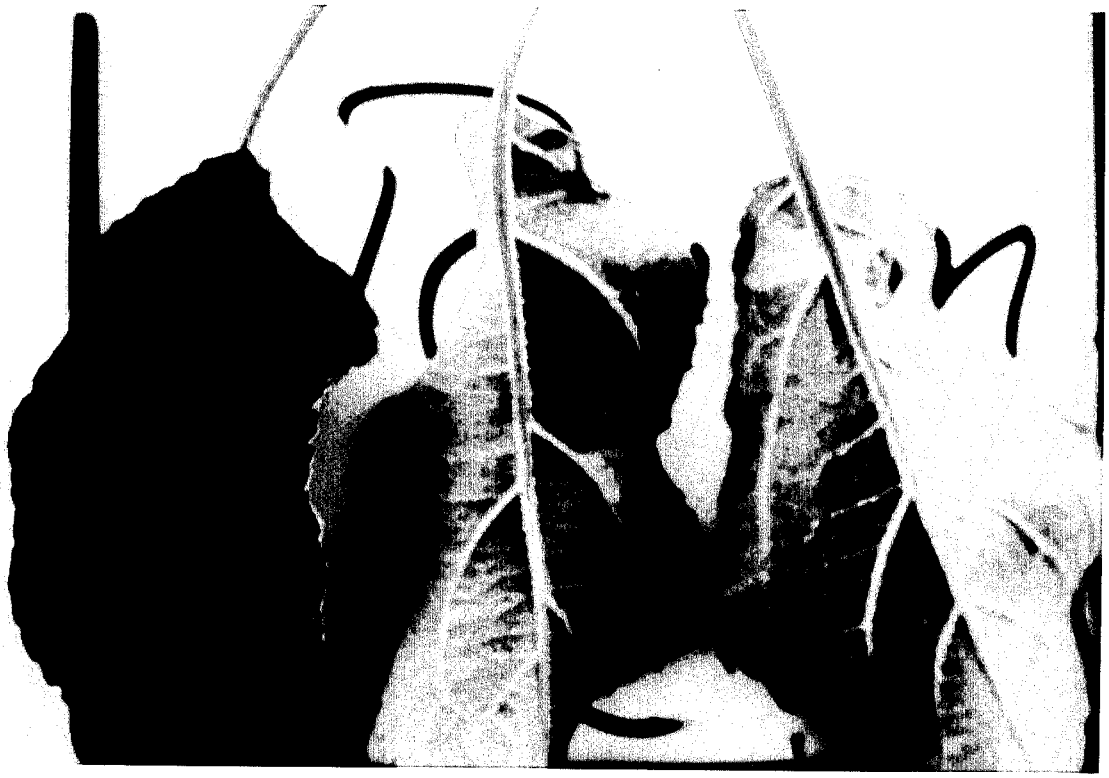

UNITED STATES PATENT AND TRADEMARK OFFICE

CERTIFICATE OF CORRECTION

PATENT NO. : Plant 07,328

DATED : September 18, 1990

INVENTOR(S) : Wilfred M. Berger

It is certified that error appears in the above-identified patent and that said Letters Patent is hereby corrected as shown below:

Column 3, line 59, "disturbed" should be --Distributed--;

Column 3, line 62, "tear" should be --year--.

Signed and Sealed this

Fifth Day of January, 1993

*Attest:*

DOUGLAS B. COMER

*Attesting Officer*

*Acting Commissioner of Patents and Trademarks*